United States Patent

Gellato et al.

[11] 4,049,516
[45] Sept. 20, 1977

[54] PHOTOCHEMICAL PROCESS FOR THE PRODUCTION OF HALOGENO-ALKANES

[75] Inventors: Michel Gellato, Billere; Jean-Louis Seris; Jeannine Suberloco, both of Pau, all of France

[73] Assignee: Societe Nationale Elf Aquitaine, Paris, France

[21] Appl. No.: 593,182

[22] Filed: July 7, 1975

[30] Foreign Application Priority Data

July 11, 1974  France .................. 74.24174

[51] Int. Cl.$^2$ ............... B01J 1/10; B01K 1/00
[52] U.S. Cl. ............... 204/158 HA; 204/163 R; 250/527
[58] Field of Search ............ 204/158 HA, 163 R; 250/527

[56] References Cited

U.S. PATENT DOCUMENTS

| 2,925,369 | 2/1960 | Grabiel et al. | 204/163 R |
| 3,424,754 | 1/1969 | Taplin | 204/158 HA |

Primary Examiner—Howard S. Williams
Attorney, Agent, or Firm—Ostrolenk, Faber, Gerb & Soffen

[57] ABSTRACT

In a photochemical process, halogeno-alkanes are produced by irradiation of an ethylenic compound and of an excess amount of bromhydric acid, the reaction being advantageously carried out in the presence of a certain amount of the halogeno-alkane compound to be obtained. The ethylenic compound concentration is of 1 mole to 1.5 mole per liter in the reaction medium; the reaction is continued until a 90% conversion is reached. 3-bromo-1-chloro-propane is obtained with a good yield by irradiation of allyl chloride and HBr. Apparatus is provided for carrying out the process batchwise and in continuous operation.

13 Claims, 1 Drawing Figure

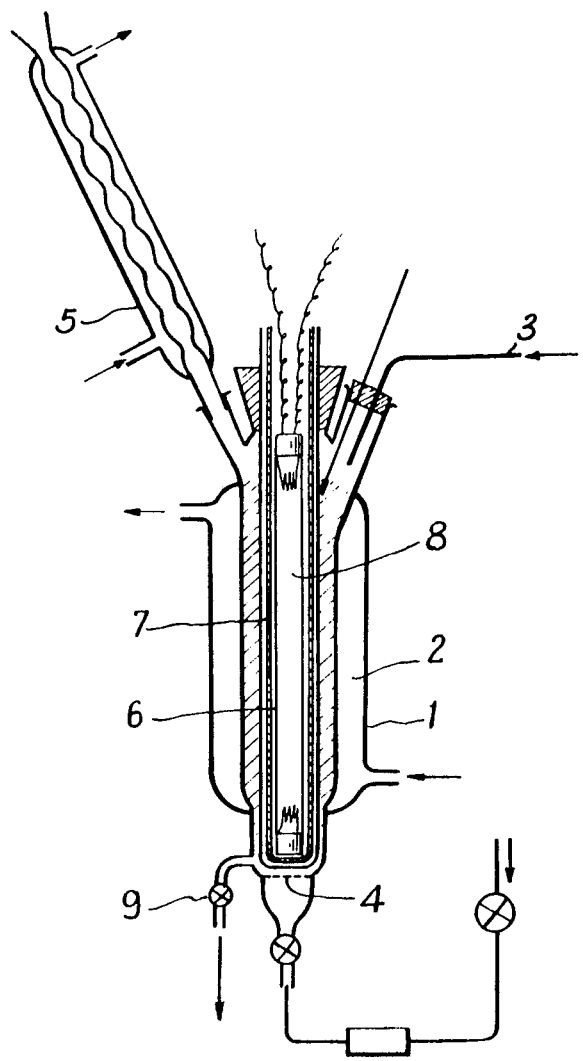

PHOTOCHEMICAL PROCESS FOR THE PRODUCTION OF HALOGENO-ALKANES

The invention relates to an improved method of hydrohalogenation of ethylenic compounds, monohalogenated or not, and more particularly to the obtention of halogeno-alkanes halogenated in the α-ω position, or only in the α position if the original ethylenic compound is not halogenated, and especially to the obtention of 3-bromo-1-chloropropane. Another object of the invention is to provide an apparatus for to carrying out the novel process.

The halogeno-alkanes, especially the α-ω dihalogenoalkanes and more particularly 3-bromo-1-chloropropane have become during the recent years highly useful and widely employed products in various industries, to wit in the fields of pharmaceuticals, pesticides, and detergents, where they are used as synthesis intermediaries. It is therefore desired to develop desired methods for their preparation. Unfortunately, the known methods and installations, using the reaction of allyl chloride and bromhydric acid, are not always satisfactory.

The chemical reaction between allyl chloride and bromhydric acid produces mainly 2-bromo-1-chloropropane, according to the Markownikov rule, if recently prepared pure reagents are used and if the reaction takes place in the darkness and in the absence of oxygen. On the contrary, the presence of small amounts of peroxides or oxygen in a mixture of allyl chloride and bromhydric acid will produce 3-bromo-1-chloropropane according to a process described by Kharasch.

It has been shown that this mechanism could be also initiated by ultra-violet light, and the formation of 3-bromo-1-chloropropane involves a photochemical addition of bromhydric acid and allyl chloride.

If the conventional method is used, i.e. the method comprising introducing, in a photochemical reactor equipped with a lamp emitting wavelengths of not more than 3000 A, bromhydric acid and allyl chloride in stoichiometric proportions, photolysis of the bromhydric acid takes place, and the radicals are added to the double bond of the allyl chloride. At the beginning of the operation the reaction is rapid, but the reaction velocity decreases very rapidly, and then becomes nil. Under these operating conditions, the allyl chloride polymerizes; the polymer deposits on the lamp-holder, thus preventing the passage of the radiations useful to the reaction.

It was therefore important to determine operating conditions enabling the allyl chloride to be photochemically treated by bromhydric acid, in order to produce 3-bromo-1-chloropropane, with a maximum yield and without the risk of the reaction being stopped due to the deposits on the lamp-holder.

The present invention overcomes the previous drawbacks; it allows allyl chloride to be converted into 3-bromo-1-chloropropane with very high yields; this invention relates to a batchwise process, but also, and more particularly, to a continuous operation process, by which 3-bromo-1-chloropropane may be prepared in large quantities, by means of an appropriate apparatus which will be described herein below.

According to the method of this invention, for producing α-ω halogeno-alkanes obtained by photochemical reaction between ethylenic compounds and bromhydric acid, and particularly 3-bromo-1-chloropropane from allyl chloride and bromhydric acid, the formation of polymer deposit from the ethylenic compound on the lamp-holder is prevented by performing the reaction within the halogeno-alkane compound and in the presence of an excess amount of bromhydric acid.

The invention is the result of the unexpected discovery, which was not obvious in view of the prior art, that the permanent presence of the halogeno-alkane compound reduces, and, under certain circumstances even entirely prevents polymer formation. As a result, the lamp is no longer covered with a more or less thick layer of polymer and is able to transform the allyl chloride into 3-bromo-1-chloropropane with maximum efficiency.

The prior art indicates that to prepare halogenated compounds by photochemical reaction of bromhydric acid and the corresponding ethylenic compound, it is possible to operate in the presence of an inert solvent. This operating procedure improves the efficiency, as well as the selectivity of the process, as regards the compound to be obtained, but the treatment of the reaction product requires the separation of the solvent by a supplementary distillation, which is not always selective when the compounds have boiling points which are close to each other.

The process of the present invention therefore constitutes a considerable improvement to, and a simplification of, the methods previously described.

For the purpose of convenience and clarity, the disclosure will only relate to the preparation of 3-bromo-1-chloropropane, it being understood that the invention is also applicable to the preparation of other α-halogenated compounds, which can bear other functions, from ethylenic compounds.

The quantities of allyl chloride which can be dissolved in 3-bromo-1-chloropropane may vary considerably, but a number of experiments have shown that the reaction velocity is maximum when the allyl chloride concentration in 3-bromo-1-chloropropane ranges from 0.1 mole to 1.5 mole per litre, preferably from 0.15 to 1 mole/litre. In other words, in a reaction medium containing 1 mole of allyl chloride per litre of solution, it is advantageous to operate until a conversion of about 90% of the allyl chloride is obtained.

For allyl chloride concentrations of 0.15 mole to 1 mole/litre, the half reaction time with bromhydric acid is about 2 minutes. It is surprising to note that for concentrations higher than 1.5 mole/litre the half reaction time increases considerably and the reaction velocity decreases very rapidly.

Another special feature of the invention consists in carrying out the allyl chloride photobromination in the presence of an excess amount of bromhydric acid. As a matter of fact, when a solution formed by the 3-bromo-1-chloropropane with, for instance, 1 mole/litre of allyl chloride dissolved in it, and then the stoichiometric amount (or the amount which can be dissolved in the medium) of bromhydric acid, are introduced into the photochemical reactor, and when this reactive mixture is irradiated, the reaction velocity of the allyl chloride is low, which can be explained by the fact that the amounts of HBr and allyl chloride present decrease simultaneously. The half reaction time is 9 minutes (and after 30 minutes only 60% allyl chloride has been converted). It is then advantageous to displace the reaction $$CH_2CH-CH_2Cl + BrH \rightarrow CH_2Br-CH_2-CH_2Cl$$

towards the right side by means of an excess amount of bromhydric acid. But as there exists a limitation on account of the HBr solubility (about 0.97 mole/litre in the allyl chloride, 0.8 mole/litre in the 3-bromo-1-chloropropane, at 22° C), it is necessary to maintain in the photochemical reactor saturation of the reaction medium by a HBr stream. This introduced stream of HBr must be such as its diffusion rate into the reaction medium is at least equal to the allyl chloride conversion rate. When operating under the conditions with a HBr stream, the half reaction time is about 25 minutes and 90% allyl chloride is converted in 30 minutes. It can be also noted that the reaction medium blackens if HBr is lacking.

The irradiation reaction of the bromhydric acid on the allyl chloride may be carried out at temperatures of from 10° C to 30° C, preferably from 15° C to 25° C, and best at 22° or 23° C. Lowering the temperature results in increasing the bromhydric acid solubility, and hence the reaction velocity, however at low temperatures the luminous efficiency of the lamp is considerably reduced; the maximum efficiency at 22–23° C is given by the average effect of these two phenomena.

Photobromination of the allyl chloride is carried out in a photochemical reactor provided with a lamp-holder equipped with a lamp emitting in the wave lengths from 2900 A to 3200 A. A low pressure mercury-vapour lamp, internally lined with a substance which re-emits by fluorescence in a wide band centered on 3000 A can be used; such a lamp also lets through an important part of the 2537 A diffraction line.

This lamp has been selected in accordance with the absorption spectrum of the various products present in the reaction medium. Bromhydric acid absorbs radiation of below 3000 A, and allyl chloride maximum radiation absorption takes place at about 2000 A. It can however be noted in the allyl chloride absorption spectrum that the 2537 A diffraction line is entirely absorbed. If the lamp is allowed to emit this line, allyl chloride polymer can be detected in the reaction medium and particularly on the lamp-holder. It is therefore necessary, according to a further aspect of the invention, to filter the lamp to eliminate the 2537 A wavelength. The filter employed is generally an aqueous solution of 50 g/litre copper sulphate. Such a filter absorbs all the photons emitted at 2537 A.

In order to still lessen the risk of allyl chloride polymerization, the photochemical reactor is preferably fitted with a large diameter lamp-holder, which reduces the photon flux per surface unit of the lamp-holder.

According to another object of the invention, lamps with an emission centred on 35000 A can be used. In that case, when the photon energy is no longer sufficient to obtain direct HBr photolysis, a sensitiser is added to the reaction medium, such as benzophenone or acetophenone.

Still according to another object of the invention it is also important to introduce into the photochemical reactor the allyl chloride solution in the 3-bromo-1-chloropropane, and to saturate said solution by HBr only in the presence of the radiation. If the saturation by HBr is carried out in the absence of the ultra-violet light, 2-bromo-1-chloropropane formation occurs, with a risk of high reaction heat.

The process of this invention can be carried out batchwise or in continuous operation, the latter being particularly advantageous for industrial applications.

The equipment for carrying out the process either batchwise or in continuous operation is essentially constituted by a photochemical reactor 1 represented on the drawing. Said reactor, made of pyrex, if of the "immersed lamp reactor" type. A fluid ensuring the thermal regulation of the reaction medium circulates in the double external jacket 2. Either the solution of allyl chloride in 3-bromo-1-chloropropane, when operating batch-wise, or the allyl chloride along when the continuous operation, is introduced through a tubulure 3. Before irradiation, bubbling of nitrogen is carried out through the sintered glass 4 at the bottom of the reactor in order to eliminate the ultimate oxygen traces detrimental to the reaction efficiency; then the gaseous bromhydric acid stream is introduced by bubbling when irradiation has begun. This HBr stream also ensures the agitation of the reaction medium during irradiation. A cooler 5 places at the reactor outlet prevents volatile products from being carried away.

The reactor includes also a lamp-holder 6 formed by a cylindrical quartz tube having a double envelope 7 into which an aqueous solution at 50 gr by litre of $So_4Cu$ is introduced. Said solution acts as a filter and absorbs the photons of 2537 A wavelength. The lamp 8 can be a 3000 A lamp (sold under the trademark of RPR) with an electric power of 15 watts. It is a low pressure mercury-vapour lamp internally lined with a substance which re-emits by fluorescence in a wide passing band, centered on 3000 A. The reaction product can be drawn off through a valve 9.

The present disclosure is related to a photochemical reactor suitable for the process, but it is in no way restrictive and many alternatives may be envisaged, depending on whether the process is carried out batchwise or in continuous operation, provided that the claimed operating conditions can be obtained.

The equipment according to the invention for carrying out in process in continuous operation includes, besides the photochemical reactor, a device for the continuous introduction of the allyl chloride and the bromhydric acid, and a device for the continuous drawing off of the reaction phase. The corresponding flow rates are calculated in order to convert 90% of allyl chloride, and to draw off a reaction phase formed by 10% of allyl chloride and 90% of other products (HBr, 3-bromo-1-chloropropane, 2-1-chloropropane, residues). The drawing off is controlled by automatic level sensor. As 3-bromo-1-chloropropane acts as a solvent, it is not necessary to introduce it with the allyl chloride. One of the distinctive features and advantages of the invention is precisely the fact that the resulting product acts, in a way, as a solvent. If, as in the prior art, another solvent were used, an allyl chloride solution would have to be continuously introduced into said solvent.

The continuously drawn-off reaction mass is treated for separating the various components.

The first component to be eliminated and recovered is the bromhydric acid. It can be contemplated to send the reaction mass to a finishing device into which an excess amount of allyl chloride is added in order to consume the bromhydric acid. Then the resulting reaction mass is sent to a series of columns for separation of the various components, or the reaction product drawn off after the photochemical reactor is degassed and the bromhydric acid is recovered in a suitable column. Then the other reaction products (allyl chloride, 3-bromo-1-chloropropane, 2-bromo-1-chloropropane and residues) are separated by distillation.

These operations for separating the various components of the reaction product should be carried out rapidly in order to reduce as far a possible the contact between allyl chloride and bromhydric acid, outside the U.V. light, and betweeen the reaction products remaining after the HBr has been removed.

The following non restrictive examples illustrate the invention. Some of these examples are used to compare the known prior art to the invention.

EXAMPLE 1

Reaction without solvent

In a photochemical reactor such as described and represented on the Figure, having a useful volume of 150 cm$^3$, 1.83 mole (150 ml = 139g) allyl chloride was introduced. The maximum bromhydric acid, i.e. 0.14 mole (11.66g) was dissolved in the allyl chloride. The reaction mixture was raised to a temperature of 22° C and the solution was irradiated. In order to compensate for the lack of bromhydric acid, a stream of HBr was introduced with a flow rate of 0.18 l/mn.

After 1 hour of irradiation, the reaction mixture was drawn off and degassed to remove the HBr in excess, and component analysis was performed. The results were the following:

allyl chloride : 11.47g(0.15 mole)
3-bromo-1-chloropropane : 215.7g (1.37 mole)
2-bromo-2-chloropropane : 7.87g (0.05 mole)
polymers and residues : 63 5g
3-bromo-1-chloropropane yield: 74 8% with respect to the involved allyl chloride.

EXAMPLE 2

Reaction in a solvent medium 150 ml of a solution in cyclohexane (i.e. a 1 mole/litre concentration) of 0.15 mole (11.47g) allyl chloride were introduced into the photochemical reactor. The amount of HBr which was dissolved in the medium, i.e. 0.06g mole, was added, while irradiating the medium, at a temperature of 22° C. At the same time, an HBr stream was bubbled through, with a flow rate of 0.8 l/mn, in order to complete the amount insufficiently dissolved in the medium, and to keep the medium saturated during the whole reaction. The half reaction time, i.e. the time necessary to transform 50% of allyl chloride was found to be 2 minutes 30 seconds. After 30 minutes of irradiation, 90% of the allyl chloride had been transformed. The reaction product was collected and degassed to remove the HBr in excess. Then the allyl chloride and the cylohexane were distillated.

The remaining reaction product was formed of 97% of 3-bromo-1-chloropropane and 3% of 2-bromo-1-chloropropane. No polymers were present. The bromo-3 chloro-1 propane yield was therefore of 87.3%.

The allyl chloride conversion could by pursued beyond 90%, but the reaction velocity becomes very low. It is therefore advisable to separate the unreacted allyl chloride and to reintroduce it into the reactor for a new operation. The solvent should also be separated by distillation.

EXAMPLE 3

The same process as in example 2 was carried out, but the cyclohexane was replaced by 3-bromo-1-chloropropane. The reaction developed in the same way. After 30 minutes of irradiation at 22° C, 90% of allyl chloride had been converted. The reaction product was degassed and the unreacted allyl chloride was distilled. The remaining product was formed by 3-bromo-1-chloropropane (solvent + formed product) and about 3% of 2-bromo-1-chloropropane. This operation has the advantage of making the solvent distillation unnecessary.

3-bromo-1-chloropropane yeild: 87%

Examples 2 and 3 show that it is advantageous to work in a solvent medium, with a concentration of 1 mole/litre of allyl chloride.

EXAMPLE 4

Bromochloropropane preparation in continuous operation

A photochemical reactor with a capacity of 165 ml was used. The reactor had the following dimensions: lamp-holder diameter: 20 mm, external diameter: 50 mm, height: 100 mm. The lamp-holder was made of quartz, the reactor itself of glass and teflon. A 3050 A lamp (sold under the trademark "Rayonnet") was used.

To start the process, the reactor was filled, through tubulure 3, with a mixture formed by 10% by mole of allyl chloride and 90% of 3-bromo-1-chloropropane. The mixture was maintained at a temperature of 20°-22° C and irradiated with, Rayonnet lamp. Then the anhydrous gaseous bromhydric acid and the allyl chloride delivered by a metering pump were introduced in continuous operation into the reactor through two separate tubulures. The pump ensured a good homogenisation of the reagents and the reaction medium.

The introduction rate of the allyl chloride was 0.6 ml/minute, that of the bromhydric acid 0.2 to 0.3 l/minute, which constituted an excess amount of HBr with respect to the stoichiometric quantity.

An equivalent amount of a reaction medium formed approximately by 10% of allyl chloride and 90% of other products : HBr, bromochloropropane (mixture of the two isomers), residues, was simultaneously drawn off through the bottom of the reactor.

The reaction mixture was conveyed either to the treatment units for separation of the products or to a finishing device and to product separation units.

With an apparatus corresponding to the described dimensions and operating method, the reactor produces per hour 1/5 of its volume isomeric bromochloropropanes.

This output value can be improved by optimising the reactor dimensions, especially by obtaining the optimum relation between the lamp-holder radius and the external radius.

In carrying out the process according to the invention, the allyl chloride conversion was deliberately limited to 90%. The 3-bromo-1-chloropropane selectivity was 97%. The efficiency thus was 87.3% with respect to the allyl chloride involved.

What is claimed is:

1. A photochemical process for producing halogeno-alkanes obtained by reacting ethylenic compounds with bromhydric acid, wherein polymers are prevented from forming and from depositing on the lamp-holder, by performing the reaction in the halogeno-alkane to be obtained, and in the presence of an excess amount of bromhydric acid sufficient to saturate the reaction medium.

2. A process according to claim 1, wherein the reaction is pursued until 90% of the ethylenic compound is converted.

3. A process according to claim 1, wherein the reaction medium contains 0.1 to 1.5 mole ethylenic compound per litre of solution.

4. A process according to claim 3, wherein the reaction is pursued until 90% of the ethylenic compound is converted.

5. A process according to claim 3, wherein the reaction medium contains 0.1 to 1 mole per litre ethylenic compound.

6. A process according to claim 1, wherein the excess amount of bromhydric acid is obtained by a permanent saturation of the reaction medium during the whole reaction, and wherein the introduction flow rate of HBr is such that its diffusion rate in the reaction medium is at least equal to the conversion rate of the ethylenic compound.

7. A process according to claim 5, wherein the ethylenic compound is allyl chloride and the obtained halogeno-alkane is 3-bromo-1-chloropropane.

8. A process accordingg to claim 6, wherein the saturation with HBr of the ethylenic compound solution is performed in the presence of the radiation.

9. A process according to claim 5, wherein the irradiation temperature ranges from 10° C to 30° C.

10. A process according to claim 9, wherein the temperature is from 15° C to 25° C.

11. A process according to claim 1, wherein the ethylenic compound is allyl chloride and the obtained halogeno-alkane is 3-bromo-1-chloropropane.

12. A process according to claim 1, wherein the irradiation temperature ranges from 10° C to 30° C.

13. A process according to claim 12 wherein the temperature is from 15° C to 25° C.

* * * * *

UNITED STATES PATENT OFFICE
CERTIFICATE OF CORRECTION

Patent No. 4,049,516     Dated September 20, 1977

Inventor(s) Michel Gellato, et al

It is certified that error appears in the above-identified patent and that said Letters Patent are hereby corrected as shown below:

In the identification of the inventors, "Suberloco" should read --Suberlucq--.

In the identification of the Assignee, "Societe Nationale Elf Aquitaine" should read --Societe Nationale Elf Aquitaine (Production)--.

Column 1, line 20, delete "desired" and read --industrial--.

Column 2, line 8, after "under" delete the comma;
line 41, after "mole" insert --to 1.5 mole--;
line 65, for "$CH_2CH-CH_2Cl$" should read --$CH_2=CH-CH_2Cl$--

Column 3, line 3, after "reactor" insert --the--;
line 67, "if" should read --is--.

Column 4, line 4, "the" (2nd occurrence) should read --in--;
line 13, "places" should read --placed--;
line 34, "in" (1st occurrence) should read --the--;
line 42, "2-1-chloropropane" should read --2-bromo-1 chloropropane--;
line 43, after "by" insert --an--.

Column 5, line 26, "74 8" should read --74.8--;
lines 50-51, "bromo-3 chloro-1 propane" should read --3-bromo-1 chloropropane--.

UNITED STATES PATENT OFFICE
CERTIFICATE OF CORRECTION

Patent No. 4,049,516           Dated September 20, 1977

Inventor(s) Michel Gellato, et al

It is certified that error appears in the above-identified patent and that said Letters Patent are hereby corrected as shown below:

Column 6, line 16, after "itself" insert --was--;
          line 22, delete the comma and insert --the--.

Column 8, line 1, "5" should read --6--;
          line 4, "accordingg" should read --according--;
          line 7, "5" should read --6--.

This certificate of correction supersedes certificate issued August 22, 1978.

Signed and Sealed this

Nineteenth Day of December 1978

[SEAL]

Attest:

RUTH C. MASON
*Attesting Officer*

DONALD W. BANNER
*Commissioner of Patents and Trademarks*